United States Patent [19]

Bargar et al.

[11] Patent Number: 4,788,301

[45] Date of Patent: Nov. 29, 1988

[54] NOVEL ALLYLIC AMINES

[75] Inventors: Thomas M. Bargar, Zionsville; Robert Broersma, Jr., Noblesville; James R. McCarthy, Zionsville, all of Ind.

[73] Assignee: Merrell Dow Pharmaceuticals Inc., Cleveland, Ohio

[21] Appl. No.: 62,813

[22] Filed: Jun. 15, 1987

Related U.S. Application Data

[63] Continuation of Ser. No. 871,638, Jun. 6, 1986, abandoned, which is a continuation of Ser. No. 687,628, Dec. 31, 1984, abandoned.

[51] Int. Cl.$^4$ .................... A61K 31/38; C07D 333/20
[52] U.S. Cl. ........................................ 514/438; 549/74
[58] Field of Search ............................ 549/74; 514/438

[56] References Cited

U.S. PATENT DOCUMENTS 4,454,158  6/1984  Bey .................................... 549/74 X

OTHER PUBLICATIONS

Columbo et al, J. Biol. Chem., vol. 259 (1984) pp. 15017–15020.
Creveling et al, Biochem. Biophys. Res. Commun., vol. 8 (1962) pp. 215–219.
Hori et al, J. Org. Chem., vol. 44 (1979) pp. 4204–4208.
Overman, J. Am. Chem. Soc., vol. 98 (1976) pp. 2901–2910.
Klemm et al, J. Org. Chem., vol. 41 (1976) pp. 2571–2579.
Aunis et al, Neurochemistry, vol. 24 (1975) pp. 425–431.
Kitz et al, J. Biol. Chem., vol. 237 (1962) pp. 3245–3249.
Kaufman et al, Pharm. Rev. (1965) vol. 17, pp. 71–100.
Pieschi et al, Pharmazie, vol. 38 (1983) pp. 335–338.
Hidaka, Nature, vol. 231 (1971) pp. 54–55.
Mangold et al, J. Biol. Chem., vol. 259 (1984) pp. 7772–7779.
Columbo et al, J. Biol. Chem., vol. 259 (1984) pp. 1593–1600.
Rajarhekan et al, J. Biol. Chem., vol. 259 (1984) pp. 6925–6930.
Fitzpatrick et al. Biochemistry, vol. 24 (1985) pp. 2108–2114.
May et al, Biochem. Biophys. Res Commun., vol. 110 (1983) pp. 161–168.
Bargar et al, Journal of Medicinal Chemistry, vol. 29 (1986) pp. 315–317.
J. B. Van der Schoot et al., Arzneimittel-Forschung, 12(9), 902 (1962).

*Primary Examiner*—Richard L. Raymond
*Attorney, Agent, or Firm*—Alice A. Brewer

[57] ABSTRACT

This invention relates to novel β-methylenethiophenethanamines which are mechanism-based inhibitors of dopamine beta-hydroxylase useful as antihypertensive agents.

4 Claims, No Drawings

NOVEL ALLYLIC AMINES

CROSS-REFERENCE TO RELATED APPLICATION

This is a continuation of application Ser. No. 871,638 filed June 6, 1986 now abandoned which is a continuation of application Ser. No. 687,628 filed Dec. 31, 1984 now abandoned.

This invention relates to novel allylic amines, the processes and intermediates useful for their preparation, and to the pharmaceutical compositions and the method of treating hypertension with such compositions.

More specifically, this invention relates to allylic amines of the formula

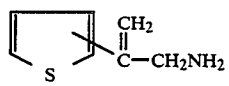

and the non-toxic pharmaceutically acceptable acid addition salts thereof. Still more specifically, the compounds of this invention relate to β-methylene-2-thiopheneethanamine and β-methylene-3-thiopheneethanamine and the non-toxic pharmaceutically acceptable acid addition salts thereof.

Representative salts are those salts formed with non-toxic organic or inorganic acids, such as, for example those formed from the following acids: hydrochloric, hydrobromic, sulfonic, sulfuric, phosphoric, nitric, maleic, fumaric, benzoic, ascorbic, succinic, methanesulfonic, acetic, propionic, tartaric, citric, lactic, malic, mandelic, cinnamic, palmitic, itaconic, and benzenesulfonic.

The allylic amines (I) of this invention can readily be prepared by a series of reactions illustrated by the following reaction scheme:

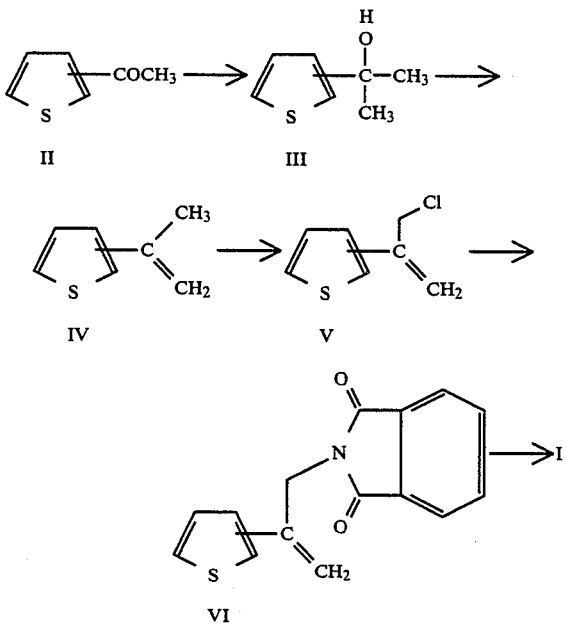

In essence, the foregoing reaction scheme depicts the conversion of 2- or 3-acetyl derivatives of thiophene to the corresponding 2- or 3-isopropylidene derivatives by reactions with methylmagnesium bromide with subsequent dehydration according to standard Grignard reaction conditions. The isopropylidene derivatives (IV) are subjected to allylic chlorination according to standard conditions and the crude products (V) are converted (via phthalimide derivatives (VI)) by the well-known Gabriel synthesis to obtain the desired allylic amines of formula I. The free bases can be converted to the acid addition salts, or the acid addition salts can be converted to the free bases, by conventional chemical methodology.

The foregoing reaction scheme is further illustrated by the following specific exemplifications.

EXAMPLE I

β-Methylene-2-Thiopheneethanamine Hydrochloride

Step A 2-(1-Methyl)ethenylthiophene

A solution of 54.0 ml (0.5 mole) of 2-acetylthiophene in 100 ml of anhydrous ether was added dropwise under $N_2$ during 1.5 hour to 211 ml of 2.85M methylmagnesium bromide/ether (0.6 mole) while the reaction mixture was stirred in an ice bath. The temperature was kept below 30° C. by controlling the rate of addition. A grey precipitate formed. The mixture was allowed to warm to 25° C. for 1 hour, then was cooled again in an ice bath while 100 ml of saturated $NaHCO_3$ solution was added carefully. The resulting mass was dissolved in about 1 liter of water and the aqueous phase was extracted twice with ether. The combined ether solutions were extracted with saturated NaCl solution, dried over $K_2CO_3$, filtered, and concentrated at atmospheric pressure to a yellow oil. To this crude alcohol was added 1.0 g of $KHSO_4$ and about 0.1 g of 4-tert-butyl catechol (inhibitor) and the mixture was placed in an oil bath maintained at 110° C. under air. After about 15 minutes, an aqueous layer formed. The cooled mixture was partitioned between ether and water and the ether layer was extracted with saturated NaCl solution, dried over $K_2CO_3$, filtered, concentrated at 1 atm. and distilled through a short Vigreux column to afford 36.0 g of colorless olefin (58%), bp 74°-78° C. at 35 torr. Similarly prepared was 3-(1-methyl)ethenylthiophene, bp 69°-79° C. at 11 torr.

Step B

N-2-(2-Thienyl)propenylphthalimide

To a solution of 12.4 g (0.1 mole) of the olefin of Step A in 50 ml of DMF was added dropwise a solution of 1.87 g (0.006 mole) of diphenyl diselenide and 16.0 g (0.12 mole) of N-chlorosuccinimide at a rate to keep the temperature below 30° C. The mixture was stirred at 25° C. for 3 hours, then was partitioned between 5% $Na_2S_2O_3$ and hexane. The hexane layer was dried over $K_2CO_3$ and concentrated at reduced pressure. The major impurity was the corresponding vinylic chloride (11%). The crude product (containing vinylic chloride) was combined with 200 ml of DMF, placed under $N_2$, and 37.0 g (0.2 mole) of potassium phthalimide was added. The magnetically stirred suspension was warmed to 90° C. for 1 hour, until TLC (hexane) showed no remaining allylic chloride. The cooled mixture was poured into 1 L of water. After 10 minutes, a brown solid separated and was filtered off, washed with water, and recrystallized from ethanol/ethyl acetate to provide a total of 26.86 g of product, mp 147.5°–149.5° C.

Anal. Calc'd for $C_{15}H_{11}NO_2S$: C, 66.90; H, 4.12; N, 5.20. Found: C, 66.81; H, 4.31; N, 5.06.

Similarly prepared was N-2-(3-thienyl)propenylphthalimide, mp. 163°–164° C.

Step C

β-Methylene-2-thiopheneethanamine HCl

To a magnetically stirred suspension of 26.9 g (0.10 mole) of the phthalimide of Step B in 400 ml of $CH_3OH$ was added 9.7 ml (0.20 mole) of hydrazine hydrate and the reaction mixture was warmed to reflux under $N_2$. After 1.5 hour, TLC (20% ethyl acetate/hexane) showed no remaining starting material. The mixture was cooled in an ice bath and the precipitated phthalhydrazide was filtered off, dissolved in in NaOH, and extracted twice with ether. The methanol filtrate was concentrated on the rotovap and the residue was partitioned between ether and 1N NaOH. The combined ether layers were extracted with one 100 ml and two 50 ml portions of 1N HCl. The combined acid layers were cooled in an ice bath and made basic by addition of solid KOH, then were saturated with NaCl and extracted three times with ether. The combined ether layers were concentrated and the residue was bulb-to-bulb distilled at 70° C., 0.07 torr to afford 10.78 of colorless liquid (77%). A solution of 6.95 g (0.05 ml) of the free base in 100 ml of ether was treated dropwise with a saturated solution of anhydrous HCl in ether until no more precipitate formed. The mixture was stirred in the ice bath for 15 minutes, then was filtered and the collected salt recrystallized from ethanol/2-propanol to yield 6.86 g of pale grey needles: mp 140°–145° C. (dec.).

Anal. Calc'd for $C_7H_9NS.HCl$: C, 47.86; H, 5.74; N, 7.97. Found: C, 47.81; H, 5.75; N, 8.08.

Similarly prepared was β-methylene-3-thiopheneethanamine hydrochloride. mp 181°–182° C.

Anal. Calc'd for $C_7H_9NS.HCl$: C, 47.86; H, 5.74; N, 7.97. Found: C, 47.68; H, 5.96; N, 7.76.

The allylic amines of this invention (I) are dopamine β-hydroxylase (DBH) inhibitors in a mechanism-based fashion; inactivation being time, concentration, and ascorbate dependent. The enzyme is inactivated directly, i.e., at the active site and thus the compounds of formula I are expected to be valuable therapeutic agents useful in the treatment of hypertension.

The dopamine β-hydroxylase inhibitory properties of the compounds of this invention can readily be determined by standard and well known procedures such as those procedures set forth in U.S. Pat. No. 4,415,191. For example, determination of whether the DBH inhibition allows time-dependent kinetics is exemplified by the procedure wherein enzymatic oxygenation by DBH is determined in aqueous solution in the presence of molecular oxygen, an electron donor such as ascorbate, and the necessary cofactors for the enzyme at a pH of 5 and a temperature of 20°–40° C., preferably 37° C. The test compound is added at the desired concentration, and the system is incubated. At different time intervals, aliquots are taken and DBH activity is measured using tyramine as the substrate and the reaction followed by measuring the oxygen uptake using a polarographic electrode and an oxygen monitor by the method of S. May et al., J. Biol. Chem. 256, 2258 (1981). The inhibition constants for the inactivation of DBH by each compound are then determined by conventional procedures such as the method of Kitz and Wilson, J. Biol. Chem. 237, 3245 (1962). When the compounds shown in Table I were tested according to the above described procedure, the DBH inhibitory activity increased as a function of the time of incubation. The initial rate of decrease of activity increased with increasing concentration of inhibitor. The results in Table I indicate that β-methylene-2-thiopheneethanamine is the more potent isomer as illustrated by the rapid rate of inactivation ($k_{inact}$) and low inhibition constant ($K_I$).

TABLE I

| DBH INHIBITORY ACTIVITY - IN VITRO | | |
|---|---|---|
| Compound | $K_I$ (mM) | $K_{inact.}$ (min$^{-1}$) |
| β-Methylene-2-Thiopheneethanamine | 2 | .02 |
| β-Methylene-3-Thiopheneethanamine | 2 | .004 |

The ability of the compounds of this invention to lower blood pressure can be determined in vivo using hypertensive rats according to standard and well known procedures. The test compound is administered intraperitoneally (ip) or orally (po) to rats and the blood pressure monitored continuously. Since DBH is a major enzyme in the synthetic pathway of the catecholamines, it would be expected that the presence of an inhibitor would act to decrease the amount of catecholamines produced, and thereby have an antihypertensive effect. The results of the testing for this anti-hypertensiveness effect are shown in Table II.

TABLE II

| Antihypertensive Activity - In Vivo | | |
|---|---|---|
| Compound | Dose mg/kg | Maximum % Change Mean Blood Pressure |
| β-Methylene-2-Thiopheneethanamine | 10 (ip) | 11 |
| | 30 (ip) | 22 |
| | 100 (ip) | 52 |
| | 50 (po) | 11 |
| | 100 (po) | 14 |
| | 200 (po) | 14 |

The compounds of this invention were conceived as mechanism-based inhibitors of DBH similar to that reported by S. May, J. Biol. Chem. 256, 2258 (1981). These compounds bear some resemblance to the catecholamines which are destroyed by the enzyme monoamine oxidase (MAO) in order to terminate neurotransmission. Because of their structural similarity to the catecholamines they may act as MAO substrates and, as such, act as k cat inhibitors of MAO. These compounds were evaluated as mechanism-based inhibitors of monooxygenasess by the method of A. Christmas et. al., Br. J. Pharmacol. 45, 490 (1972). The potent DBH inhibitory activity against the weak MAO inhibitory activity of β-methylene-2-thiopheneethanamine is shown in Table III.

TABLE III

| DBH vs. MAO Inhibition |
|---|
| Effect on purified DBH |
| Time-dependant inhibition t1/2 = 7 min at $5.10^{-5}$ M final concentration |
| Effect on Rat Brain - Mitochondrial MAO |
| Weak time-dependant MAO inhibitor MAO A Ki $3.2 \times 10^{-4}$ M τ = Tau$_{50}$ 2.6 min MAO B Ki $1.1 \times 10^{-4}$ M τ = Tau$_{50}$ 4.9 min |

Thus, based upon these and other standard laboratory techniques known to evaluate dopamine β-hydroxylase inhibitors, by standard toxicity tests and by standard pharmacological assay for the determination of antihypertensive activity in mammals, and by comparison of these results with the results with known antihypertensive agents, the effective antihypertensive dosage of the compounds of this invention can readily be determined. In general, effective antihypertensive results can be achieved at a dose of about 5 to about 100 mg per kilogram of body weight per day. Of course the specific initial and continuing dosage regimen for each patient will vary according to the nature and severity of the hypertension as determined by the attending diagnostician.

In their function as therapeutically useful compounds, it is advantageous to administer the compounds to the host animal in admixture with an acceptable pharmaceutical carrier suitable for enteral or parenteral administration, said carrier constituting a major portion of the admixture. Such preparations may be in such forms as, for example, tablets, capsules and suppositories, or in liquid forms, as for example, elixirs, emulsions, sprays and injectables. In the formulatio of pharmaceutical preparations there can be employed such substances which do not react with active substance as, for example, water, gelatin, lactose, starches, magnesium sterate, talc, vegetable oils benzyl alcohols, gums, polyalkylene glycols, petroleum jelly and the like. The active ingredient of such pharmaceutical preparations is preferably present in the preparation in such proportions by weight that the proportion by weight of the active ingredient to be administered lies between 0.1% and 50%.

We claim:

1. A compound of the formula

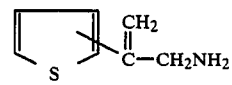

and the non-toxic pharmaceutically acceptable acid addition salts thereof.

2. A compound of claim 1, said compound being β-methylene-2-thiopheneethanamine.

3. A compound of claim 1, said compound being β-methylene-3-thiopheneethanamine.

4. A method of treating hypertension in mammals which comprises administering to said mammal an effective amount of an allylic amine of claim 1.

* * * * *